United States Patent [19]

Grubbs et al.

[11] Patent Number: 4,473,085
[45] Date of Patent: Sep. 25, 1984

[54] FLAVOR-RELEASE β-HYDROXY-ESTER COMPOSITIONS

[75] Inventors: Harvey J. Grubbs, Mechanicsville; Yoram Houminer, Richmond, both of Va.

[73] Assignee: Philip Morris Incorporated, New York, N.Y.

[21] Appl. No.: 259,264

[22] Filed: Apr. 30, 1981

[51] Int. Cl.³ .................... A24B 3/12; A24B 3/36; A24B 3/38; A24B 3/40
[52] U.S. Cl. ................................ 131/276; 131/277; 560/60
[58] Field of Search .................. 131/275, 276, 279; 560/60; 252/522 A

[56] References Cited

U.S. PATENT DOCUMENTS 4,312,368  1/1982  Houminer et al. ............... 131/277

Primary Examiner—V. Millin
Assistant Examiner—Gregory Beaurage
Attorney, Agent, or Firm—Arthur I. Palmer, Jr,; George E. Inskeep; D. Anthony Gregory

[57] ABSTRACT

This invention provides tobacco compositions which contain a hydroxy-substituted carboxylate compound as a flavorant additive.

In one of its embodiments, this invention provides tobacco compositions which contain a hydroxy-substituted alkanoate flavorant additive such as ethyl 2-(2-butyl)-3-hydroxy-3-methyl-3-phenylpropionate:

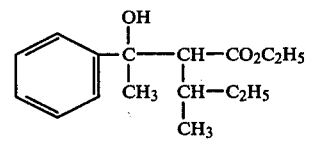

Under smoking conditions the above illustrated hydroxy-substituted alkanoate additive and its pyrolysis products flavor the mainstream and sidestream smoke.

14 Claims, No Drawings

FLAVOR-RELEASE β-HYDROXY-ESTER COMPOSITIONS

BACKGROUND OF THE INVENTION

There has been increased interest in organic materials which can function as flavoring agents for modifying or improving the flavor and aroma of tobaccos, foodstuffs, beverages and other such consumer products.

U.S. Pat. No. 3,402,051 describes a process for imparting a popcorn-like flavor and aroma to tobacco and foodstuffs by the incorporation of a 2-acetylpyrazine derivative therein.

Other patents which disclose the addition of various pyrazine compounds to tobacco and foodstuffs as a means of providing flavor or flavor enhancement include U.S. Pat. Nos. 3,684,809; 3,705,158; 3,754,934; 3,764,349; 3,767,426; and 3,881,025.

U.S. Pat. No. 3,914,227 discloses pyridyl and pyrazyl ketones and their use in altering the organoleptic properties of tobacco and foodstuffs, and U.S. Pat. No. 4,166,869 discloses acylpyrimidines useful as flavorants for the same type of applications.

Alkylpyridines have also been found to be useful tobacco additives. As for example, U.S. Pat. No. 3,625,224 describes the use of methylpyridines, ethylpyridines and various dialkylpyridines as tobacco additives. U.S. Pat. No. 3,381,691 discloses 2-methyl-5-isopropylpyridine as a tobacco additive.

It is characteristic of pyridine, pyrazine, pyrimidine and other heterocyclic derivatives employed as tobacco flavorants in the prior art, as illustrated by the above described technical literature, that the respective heterocyclic derivatives have the disadvantage of both high volatility and low odor threshold. Both of these properties significantly restrict the extent that these heterocyclic derivatives can be utilized as flavorants in tobacco compositions. A quantity of a pyrazine or pyridine derivative in a tobacco composition sufficient to have a noticeable effect in low delivery cigarettes causes a marked pack aroma.

In a similar manner, the incorporation in tobacco of flavorants in the form of clathrates has been found to be unsatisfactory, since the yield of flavor when tobacco containing such clathrates is burned is very low. Likewise, the yield of flavorant is low when an ester such as menthyl succinate or menthyl borate is incorporated into a tobacco composition that is subsequently burned.

When an aldehyde flavorant such as cinnamaldehyde is added to a smoking composition, the loss of the flavorant during the manufacturing process and during storage is high, due to the relatively high vapor pressure of the aldehydic compound.

Further, as described in U.S. Pat. No. 3,782,391 alkyl esters of beta-methylvaleric acid are known to impart a fruity, apple-like aroma and a nut-like flavor when incorporated in tobacco. However, as noted in U.S. Pat. No. 3,854,485, such flavorant compounds are relatively volatile substances with a low odor threshold, and they present an evaporation problem in prolonged storage of the flavored tobacco compositions. Other esters such as monoalkyl and dialkyl malonates are known to provide tobacco smoke with a fermented apple-peel and walnut-like flavor and aroma, but such esters yield only a limited form of flavor enhancement in tobacco products.

U.S. Pat. No. 4,036,237 endeavors to overcome some of the disadvantages of the above-described flavorant technology. The said patent provides for the incorporation in smoking compositions of a flavorant compound which is not lost during the manufacture and storage of the flavored smoking composition, and which releases cherry-like or fruity flavor to the smoke thereof when the smoking composition is burned. Illustrative of a U.S. Pat. No. 4,036,237 flavorant compound is ethyl 2,2-dimethyl-3-hydroxy-3-phenylpropionate.

There remains a need for smoking compositions with enhanced flavor and aroma that do not exhibit the various disadvantages of prior art smoking compositions which contain a relatively volatile compound as a flavorant additive.

Accordingly, it is a main object of this invention to provide tobacco and non-tabacco smoking compositions which have incorporated therein a flavorant additive which is characterized by low volatility and low pack aroma.

It is another object of this invention to provide smoking compositions of tobacco and non-tobacco materials and blends thereof, containing a hydroxy-substituted carboxylate flavorant additive, which smoking compositions are adapted to impart flavor and aroma to the mainstream and sidestream smoke under smoking conditions.

It is a further object of this invention to provide novel hydroxy-substituted carboxylate compounds which can be subjected to pyrolysis conditions to release carbonyl and ester constituents which can enhance the flavor and aroma of smoking compositions and foodstuffs.

Other objects and advantages of the present invention shall become apparent from the accompanying description and examples.

This patent application is related to patent application Ser. No. 122,901, filed Feb. 20, 1980, now U.S. Pat. No. 4,312,368.

DESCRIPTION OF THE INVENTION

One or more objects of the present invention are accomplished by the provision of a smoking composition which comprises an admixture of (1) combustible filler selected from natural tobacco, reconstituted tobacco and non-tobacco substitutes, and (2) between about 0.00001 and 2 weight percent, based on the total weight of filler, of a hydroxy-substituted carboxylate compound corresponding to the formula:

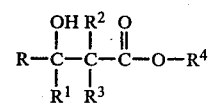

wherein R and $R^1$ are substituents selected from aliphatic, alicyclic and aryl groups containing between about 1–12 carbon atoms; $R^2$ and $R^3$ are hydrogen or substituents selected from aliphatic, alicyclic and aromatic groups containing between about 1–12 carbon atoms; and R and $R^1$ or $R^2$ and $R^3$, respectively, when taken together with connecting elements form an alicyclic structure; and $R^4$ is a substituent selected from aliphatic, alicyclic and aromatic groups containing between about 1–12 carbon atoms.

With respect to R and $R^1$, the term "alicyclic" is meant to exclude heterocyclic substituents. With respect to $R^2$ $R^3$ and $R^4$, the term "alicyclic" is meant to include heterocyclic substituents.

Illustrative of the R and $R^1$ substituents in the formula represented above are groups which include methyl, propenyl, butyl, pentyl, hexenyl, methoxyethyl, acetyl, cyclopropyl, cyclobutyl, cyclopentyl, cyclohexyl, menthyl, phenyl, tolyl, xylyl, benzyl, phenylethyl, methoxyphenyl, naphthyl, and the like. $R^2$, $R^3$ and $R^4$ can be groups of the type recited above, but in addition can be heterocyclic groups such as furyl, tetrahydrofuryl, piperidyl, pyrrolidyl, pyrazolyl, pyridyl, pyridazyl, pyrimidyl, pyrazyl, and the like.

As noted previously, R and $R^1$ or $R^2$ and $R^3$, respectively, when taken together with the connecting elements form an alicyclic group such as cyclopentyl, cyclohexyl, cycloheptyl, menthyl, and the like.

A hydroxy-substituted carboxylate compound (i.e., a β-hydroxy-ester) corresponding to the formula represented above is a low volatility flavorant which under normal smoking conditions, or other comparably intensive localized heating conditions pyrolyzes into products which exhibit flavorant properties. These secondary flavorant compounds are released in accordance with the following illustrated reaction mechanism:

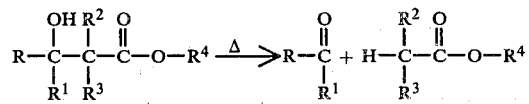

Each of the pyrolysis products illustrated above can impart flavor and aroma to tobacco and non-tobacco smoke under smoking conditions.

As demonstrated in the Examples, a present invention β-hydroxy-ester (i.e., one in which neither of R and $R^1$ is hydrogen) is more reactive under pyrolysis conditions than a β-hydroxy-ester of the type disclosed in U.S. Pat. No. 4,036,237 (i.e., one in which one of R and $R^1$ is hydrogen). A present invention ester (I) does not have a β-hydrogen substituent as does a U.S. Pat. No. 4,036,237 ester (II):

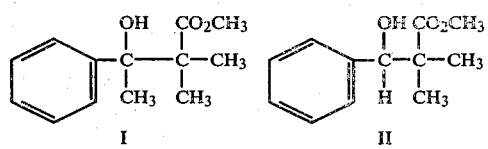

Because of the higher reactivity of a present invention β-hydroxy-ester (e.g., compound I above), and its susceptibility to retro-aldol cleavage, a lower pyrolysis temperature is required in comparison with a U.S. Pat. No. 4,036,237 type β-hydroxy-ester (e.g., compound II above). Overall there are less side reactions such as dehydration and less tar formation with a present invention β-hydroxy-ester. Hence, a present invention β-hydroxy-ester such as compound I above is a more efficient flavor-release agent (e.g., as a tobacco flavorant) than is the U.S. Pat. No. 4,036,237 compound II above. The same reasoning applies to a prior art compound such as methyl 2-isopropyl-5-methyl-3-hydroxyhexanoate which is disclosed in Example XI of U.S. Pat. No. 3,704,714.

PREPARATION OF HYDROXY-SUBSTITUTED CARBOXYLATE COMPOUNDS

One method of preparing the hydroxy-substituted carboxylate compounds of the present invention is by the reaction of an alkanoate derivative with a carbonyl derivative, both of which derivatives are appropriately substituted in a manner as previously defined:

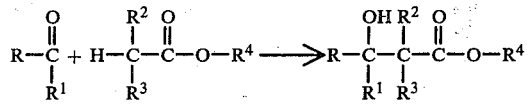

The reaction is conducted in the presence of a strong base such as lithium diisopropylamide, or alkali metal hydride. The strong base initiates the in situ formation of an anion intermediate:

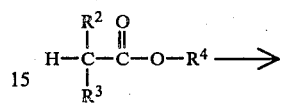

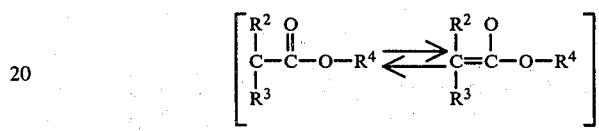

Preferably, the base is added to the alkanoate starting material in an inert solvent medium maintained at a temperature between about $-80°$ C. and $50°$ C. and under an inert atmosphere. This procedure is followed by the addition of the carbonyl compound to the reaction medium at a temperature between about $-80°$ C. and $25°$ C.

Another method of preparing the hydroxy-substituted carboxylate compounds of the present invention is by means of a Reformatsky-type reaction [R. L. Shriner, Organic Reactions, Vol. I, pp 1–37. John Wiley & Sons, Inc. New York (1942)], which may be generalized as follows with appropriately substituted starting materials.

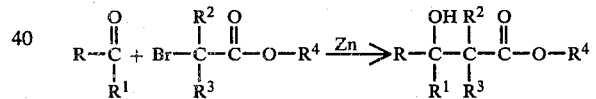

The first method of preparation described above has advantages over the Reformatsky method of preparation, since the first method does not require a costly bromine-containing ester co-reactant, and it permits a greater latitude in selection of the ester co-reactant.

The resultant hydroxy-substituted carboxylate addition products obtained by either of the two preparative methods illustrated above are odorless, normally liquid compounds of high boiling point.

PREPARATION OF TOBACCO COMPOSITIONS

The present invention smoking compositions can be prepared by admixing natural tobacco and/or reconstituted tobacco and/or a non-tobacco substitute with between about 0.00001 and 2 weight percent based on the weight of the smoking composition, of a flavorant additive which corresponds to one of the structural formulae set forth hereinabove in definition of the hydroxy-substituted carboxylate compounds.

The invention hydroxy-substituted carboxylate flavorant additive can be incorporated into the tobacco in accordance with methods known and used in the art. Preferably the flavorant additive is dissolved in a solvent such as water, alcohol, or mixtures thereof, and then sprayed or injected into the tobacco or non-tobacco substitute matrix. Such method ensures an even distribution of the flavorant additive throughout the tobacco, and thereby facilitates the production of a more uniform smoking composition. Alternatively, the flavorant may be incorporated as part of a concentrated tobacco extract which is applied to a fibrous tobacco web as in the manufacture of reconstituted tobacco. Another suitable procedure is to incorporate the flavorant in tobacco or non-tobacco substitute filler in a concentration between about 0.5–5 weight percent, based on the weight of filler, and then subsequently to blend the treated filler with filler which does not contain flavorant additive.

The term "non-tobacco substitute" is meant to include smoking filler materials such as are disclosed in U.S. Pat. Nos. 3,529,602; 3,703,177; 3,796,222; 4,019,521; 4,079,742; and references cited therein, incorporated herein by reference.

Illustratively, U.S. Pat. No. 3,529,602 describes a burnable sheet which may be used as a tobacco substitute, which sheet contains ingredients which include (1) a film-forming ingredient comprising a pectinaceous material derived from tobacco plant parts and having an acid value in excess of 30 milligrams of potassium hydroxide per gram, and (2) a mineral ingredient comprising an alkali metal salt, an alkaline earth metal salt or a clay.

U.S. Pat. No. 3,703,177 describes a process for preparing a non-tobacco smoking product from sugar beet pulp, which process involves the acid hydrolysis of the beet pulp to release beet pectins, and at least an alkaline earth treatment thereafter to cause crosslinking of the pectins and the formation of a binding agent for the exhausted beet matrix.

U.S. Pat. No. 3,796,222 describes a smoking product derived from coffee bean hulls. The hulls are treated with reagents that attack the alkaline earth metal crosslinks causing the release of the coffee pectins. The pectins act as a binding agent and together with the treated hulls may be handled and used similarly to a tobacco product.

U.S. Pat. No. 4,019,521 discloses a process for forming a smoking material which involves heating a cellulosic or other carbohydrate material at a temperature of 150°–750° C. in an inert atmosphere for a period of time sufficient to effect a weight loss of at least 60 percent but not more than 90 percent.

U.S. Pat. No. 4,079,742 discloses a process for the manufacture of a synthetic smoking product from a cellulosic material, which process involves a pyrolysis step and a basic extraction step to yield a resultant matrix which has a tobacco-like brown color and has improved smoking characteristics.

With respect to the quantity of substituted carboxylate compound employed as a flavorant in the invention smoking compositions, it is to be noted that as little as 0.00001 percent, based on the total weight of filler, produces pyrolysis products which can be detected subjectively by an experienced smoking panel. This is a unique and unexpected aspect of the type of flavorant employed in the invention tobacco compositions, for the reason that comparative prior art tobacco flavorants are not known to exhibit this unusual degree of organoleptic potency. The high potency of an invention flavorant compound is advantageous since it permits the use of an exceptionally small quantity of the said flavorant in a smoking composition for the purpose of imparting flavor and aroma to the mainstream and sidestream smoke under smoking conditions. It is particularly noteworthy that the flavorant pyrolysis products can be detected subjectively by an experienced smoking panel, notwithstanding that the pyrolysis products are derived from a flavorant which is present in the smoking composition in a parts per million range which is difficult to detect by conventional analytical methods.

In another embodiment, the present invention also contemplates the incorporation of one of the hydroxy-substituted carboxylate compounds described above into an article of manufacture which is burned under controlled conditions within the environment of a human habitat. In particular, the combustible articles contemplated are those such as candles, room deodorizers, manufactured fireplace fuel, and the like, the buring of which evolves a gaseous effluent which can be sensed by individuals within olfactory proximity. As it is apparent, wood logs can also be treated with a solution of a hydroxy-substituted carboxylate compound prior to ignition in a fireplace.

The incorporation of between about 0.001 and 10 weight percent of a hydroxy-substituted carboxylate compound of the present invention into a candle, for example, can introduce a pleasant aroma or fragrance into a confined living space when the candle is lighted.

In a further embodiment, the present invention provides a method for improving the flavor of a foodstuff (e.g., a meat-containing or meat-simulating product) which comprises contacting the foodstuff with a non-toxic gaseous effluent which is generated by the burning of a combustible material (e.g., a solid fuel) having admixed therewith between about 0.0001 and 10 weight percent, based on the weight of combustible content, of a hydroxy-substituted carboxylate compound of the present invention. Illustrative of one of the applications contemplated is the incorporation of the hydroxy-substituted carboxylate compound in a smoke-house system for curing meats. Also, an invention hydroxy-substituted carboxylate compound can be incorporated in manufactured carbonaceous fuels (e.g., charcoal briquettes) which are used for broiling raw meat and fish products. As it is apparent, a present invention β-hydroxy-ester can be employed with optimal advantage in any application for adding flavor or enhancing the flavor of a foodstuff in which the foodstuff is subjected to a cooking cycle. The said hydroxy-substituted carboxylate compound can be admixed with or applied to the surface of foodstuffs prior to or during the cooking phase. The carboxylate compound can be blended with edible solids or liquids to facilitate its application as a flavorant additive. A blend of between about 0.01 and 10 weight percent of carboxylate compound in vegetable oil, for example, is a convenient medium for imparting flavor to foodstuffs in deep-fry operations.

An invention β-hydroxy-ester can also be incorporated as a flavorant additive in prepared sauces, gravies and dressings. Suitable edible vehicles or carriers for a present invention β-hydroxy-ester compound include fats and oils such as cottonseed oil, soy bean oil, olive oil, and peanut oil; emulsified fats and oils such as butter and margarine; gums such as guar, locust bean, gum arabic, carageenen; and the like.

The following examples are further illustrative of the present invention. The reactants and other specific ingredients are presented as being typical, and various modifications can be derived in view of the foregoing disclosure within the scope of the invention.

EXAMPLE I

Preparation And Pyrolysis Of Ethyl 2-Propyl-3-hydroxy-3-methyl-3-phenylpropionate

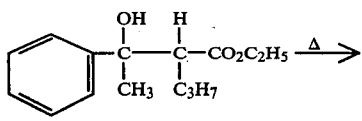

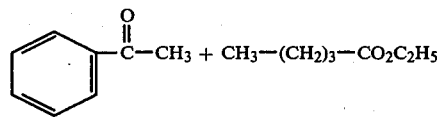

To a solution of diisopropylamine (11.1 grams, 0.11 mole) in anhydrous ether (200 milliliters) at −78° C. under nitrogen and with stirring is added a solution of butyllithium (0.11 mole) in hexane (44 milliliters). The resulting mixture is stirred at −78° C. for 15 minutes.

A solution of ethyl valerate (13.0 grams, 0.1 mole) in ether (40 milliliters) is added with stirring over a period of about 2 minutes, and the mixture is stirred at −78° C. for an additional 20 minutes. To the above solution at −78° C. with stirring is added a solution of acetophenone (12.0 grams, 0.1 mole) in ether (50 milliliters) and the mixture is stirred at −78° C. for 15 minutes. A 10% HCl solution (70 milliliters) is added with stirring and the mixture is allowed to warm up to room temperature.

The organic layer is separated, washed with water, dried ($MgSO_4$) and evaporated under reduced pressure. The liquid so obtained is distilled in a Kugelrohr apparatus to yield 12.4 grams (50%) of the pure product, b.p. 80° C. (air bath temperature) at 0.05 mm Hg. I.R., N.M.R. and M.S. data confirm the above structure.

Analysis calculated for $C_{15}H_{22}O_3$: C, 71.97; H, 8.86. Found: C, 72.01; H, 8.99.

A 10 milligram sample of the prepared hydroxy-ester is pyrolyzed is an open tube at 250° C. for 5 minutes. Examination of the pyrolyzate by G.C., L.C. and T.L.C. indicates >90% decomposition to form a 1:1 mixture of acetophenone and ethyl valerate.

EXAMPLE II

Preparation And Pyrolysis Of Methyl 2,2-Dimethyl-3-hydroxy-3-methyl-3-phenylpropionate

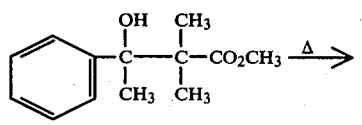

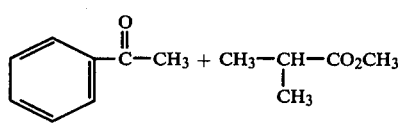

The reaction of acetophenone (6.0 grams, 0.05 mole) with the enolate of methyl isobutyrate (5.1 grams, 0.05 mole) is conducted in the manner described in Example I. Distillation yields 8.2 grams (74%) of the pure hydroxy-ester, b.p. 65°–70° C. (air bath temperature) at 0.025 mm Hg. I.R. and N.M.R. data confirm the above structure.

A 50 milligram sample of the hydroxy-ester is pyrolyzed in a sealed tube at 200° C. for 30 minutes. Analysis of the pyrolysate by liquid chromatography indicates that 100% of the hydroxy-ester has been decomposed to yield a 1:1 mixture of acetophenone and methyl isobutyrate. The same pyrolysis at 240° C. for 2 minutes results in >90% decomposition of the hydroxy-ester.

EXAMPLE III

Preparation And Pyrolysis Of Ethyl 2-(2-Butyl)-3-hydroxy-3-methyl-3-phenylpropionate

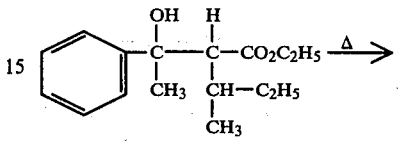

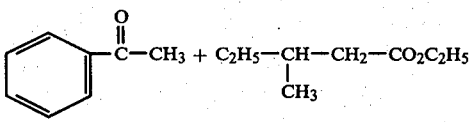

The reaction of acetophenone (12 grams, 0.1 mole) with the enolate of ethyl 3-methylvalerate (14.4 grams, 0.1 mole) is carried out in the manner described in Example I. Distillation yields 9.5 grams (36%) of the pure product, b.p. 75°–80° C. (air bath temperature) at 0.05 mm Hg. I.R., N.M.R. and M.S. data confirm the above structure.

Analysis calculated for $C_{16}H_{24}O_3$: C, 72.69; H, 9.15. Found: C, 72.91; H, 9.22.

A 310 milligram sample of the prepared hydroxy-ester is heated in an open test tube at 250° C. for 5 minutes. By means of preparative thin layer chromatography 40 milligrams of unreacted starting material are recovered. Gas chromatography analysis indicates that >80% of hydroxy-ester has been converted into a 1:1 mixture of acetophenone and ethyl 3-methylvalerate.

EXAMPLE IV

Preparation And Pyrolysis Of Ethyl 2-Isopropyl-3-hydroxy-3-methyl-3-phenylpropionate

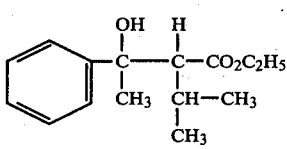

The reaction of acetophenone (6.0 grams, 0.05 mole) with the enolate of ethyl isovalerate (6.5 grams, 0.05 mole) is carried out as described in Example I. Distillation gives 6.8 grams (54%) of the pure product, b.p. 65°–70° C. (air bath temperature) at 0.025 mm Hg. I.R. and N.M.R. data confirm the above structure.

Analysis calculated for $C_{15}H_{22}O_3$: C, 71.97; H, 8.86. Found: C, 72.06; H, 8.88.

The material undergoes smooth pyrolysis when injected into a gas chromatography column (at about 230° C.) to generate acetophenone and ethyl isovalerate.

EXAMPLE V

Preparation And Pyrolysis Of Ethyl 2-(2-Butyl)-3-hydroxy-3-methylnonanoate

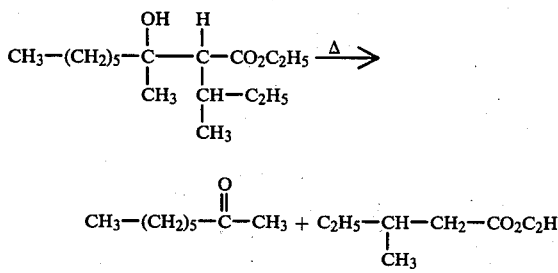

The reaction of 2-octanone (128 grams, 1 mole) with the enolate of ethyl 3-methylvalerate (144 grams, 1 mole) is conducted in the manner described in Example I. Distillation yields 154 grams (57%) of the pure product, b.p. 90°–94° C. at 0.05 mm Hg. I.R., N.M.R. and M.S. data confirm the above structure.

Analysis calculated for $C_{16}H_{32}O_3$: C, 70.54; H, 11.84. Found: C, 70.68; H, 11.94.

A sample of the prepared hydroxy-ester pyrolyzes at 230° C. to a 1:1 mixture of 2-octanone and ethyl 3-methylvalerate.

EXAMPLE VI

Preparation And Pyrolysis Of Ethyl 2-(2-Butyl)-3-hydroxy-3-methyldodecanoate

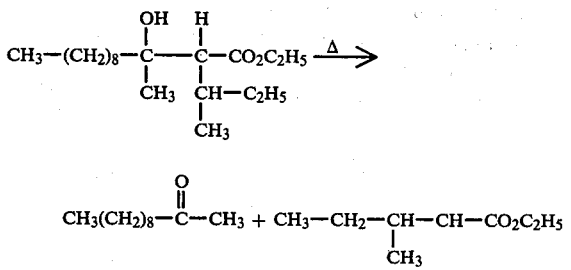

The reaction of 2-undecanone (17.0 grams, 0.1 mole) with the enolate of ethyl 3-methylvalerate (14.4 grams, 0.1 mole) is carried out as described in Example I. Distillation gives 6.3 grams (20%) of the pure hydroxy-ester, b.p. 100° C. (air bath temperature) at 0.05 mm Hg. I.R. and N.M.R. data confirm the above structure.

Pyrolysis of a sample of the prepared hydroxy-ester at about 300° C. for 2 minutes yields a 1:1 mixture of 2-undecanone and ethyl 3-methylvalerate.

EXAMPLE VII

Preparation And Pyrolysis Of Ethyl 2-Propyl-3-hydroxy-3-phenylpropionate

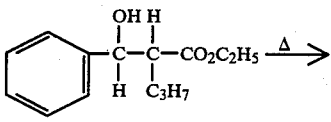

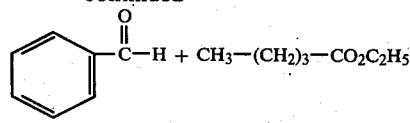

The reaction of benzaldehyde (5.3 grams, 0.05 mole) with the enolate of ethyl valerate (6.5 grams, 0.05 mole) is conducted in accordance with the procedure described in Example I. Distillation yields 6.9 grams (58%) of the pure product, b.p. 70°–80° C. (air bath temperature) at 0.05 mm Hg. I.R. and N.M.R. data confirm the above structure.

Analysis calculated for $C_{14}H_{20}O_3$: C, 71.16; H, 8.53. Found: C, 71.13; H, 8.70.

A 100 milligram sample of the prepared hydroxy-ester is pyrolyzed in a sealed tube at 240°–245° C. for 1 hour. Examination of the pyrolyzate by liquid chromatography indicates that it consists of 60% of unreacted hydroxy-ester and 40% of a 1:1 mixture of ethyl valerate and benzaldehyde.

Ethyl 2-propyl-3-hydroxy-3-phenylpropionate of this Example corresponds to the hydroxy-ester formula disclosed in U.S. Pat. No. 4,036,237. This prior art hydroxy-ester differs from the present invention ethyl 2-propyl-3-hydroxy-3-methyl-3-phenylpropionate of Example I in that it contains a β-hydrogen substituent rather than a β-methyl substituent.

Simultaneous pyrolysis studies conducted at 235°–240° C. indicate that the hydroxy-ester described in Example I is at least 8 times more reactive than that described in the present Example VII. Therefore, the pyrolysis results reported in this Example as compared to those in Example I demonstrate the higher efficiency of the Example I invention compound as a flavor-release agent.

EXAMPLE VIII

Preparation And Pyrolysis Of Methyl 2,2-Dimethyl-3-hydroxy-3-phenylpropionate

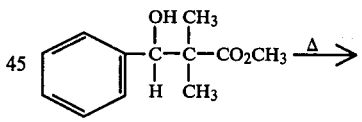

The reaction of benzaldehyde (10.6 grams, 0.1 mole) with the enolate of methyl isobutyrate (10.2 grams, 0.1 mole) is carried out as described in Example I. Recrystallization of the crude reaction product from ethanol yields needles (18.5 grams, 89%) of the pure hydroxy-ester, m.p. 69°–70° C. I.R. and N.M.R. data confirm the above structure.

Analysis calculated for $C_{12}H_{16}O_3$: C, 69.21; H, 7.74. Found: C, 69.17; H, 7.84.

A 50 milligram sample of the prepared hydroxy-ester is pyrolyzed in a sealed tube at 200° C. for 30 minutes. Analysis of the pyrolyzate by liquid chromatography indicates the following composition: 93% of unreacted starting material and 7% of a 1:1 mixture of benzaldehyde and methyl isobutyrate.

Methyl 2,2-dimethyl-3-hydroxy-3-phenylpropionate of this Example is disclosed in U.S. 4,036,237 (Compound F, Example 6). This prior art hydroxy-ester differs from the present invention methyl 2,2-dimethyl-3-hydroxy-3-methyl-3-phenylpropionate of Example II in that it contains a 62-hydrogen substituent rather than a β-methyl substituent.

Simultaneous pyrolysis studies conducted at both 180° C. and 200° C. indicate that the hydroxy-ester described in Example II is at least 50 times more reactive than that described in the present Example VIII. Therefore, the pyrolysis results reported in this Example as compared to those reported in Example II demonstrate the much higher efficiency of the Example II invention compound as a flavor-release agent.

EXAMPLE IX

Employing the same general preparative method of Example I, the following β-hydroxy-esters are prepared.

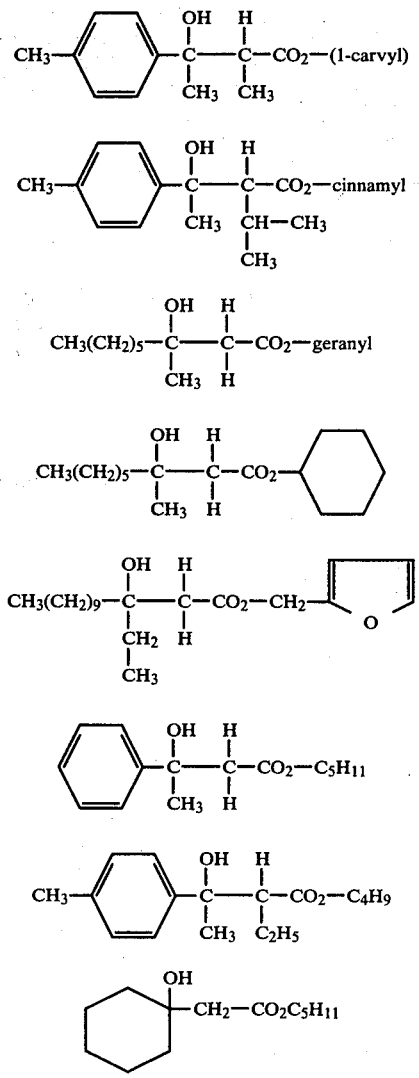

Pyrolysis of the respective β-hydroxy-esters yields a retro-aldol 1:1 mixture of ketone and ester cleavage products.

Referring to the general formula:

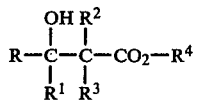

the most efficient flavor-release β-hydroxy-esters under pyrolysis conditions are those in which one of R and $R^1$ is aryl and the other is alkyl, and both $R^2$ and $R^3$ are alkyl.

The next most efficient type of flavor-release β-hydroxy-esters under pyrolysis conditions are those in which one of R and $R^1$ is aryl and the other is alkyl, $R^2$ is hydrogen and $R^3$ is alkyl.

EXAMPLE X

Preparation Of A Smoking Composition Containing An Invention β-Hydroxy-ester Flavorant Cigarettes are fabricated employing a blend of tobaccos treated with an ethanolic solution of ethyl 2-(2-butyl)-3-hydroxy-3-methyl-3-phenylpropionate to provide 0.0001% of the compound by weight of the tobacco. The cigarettes are targeted to deliver 8 mg of tar per cigarette.

Untreated controls are prepared and the treated cigarettes are compared to the controls by an experienced smoking panel. The treated cigarettes are found to have a distinct fruity note and more response as compared to the controls.

Similar results are obtained with the β-hydroxy-esters disclosed in Example I–VI and IX.

What is claimed is:

1. A smoking composition comprising an admixture of (1) combustible filler selected from natural tobacco, reconstituted tobacco and non-tobacco substitutes, and (2) between about 0.00001 and 2 weight percent, based on the total weight of filler, of a hydroxy-substituted carboxylate compound corresponding to the formula:

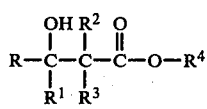

wherein R and $R^1$ are substituents selected from aliphatic, alicyclic and aryl groups containing between about 1–12 carbon atoms; $R^2$ and $R^3$ are hydrogen or substituents selected from aliphatic, alicyclic and aromatic groups containing between about 1–12 carbon atoms; and R and $R^1$ or $R^2$ and $R^3$, respectively, when taken together with connecting elements form an alicyclic structure; and $R^4$ is a substituent selected from aliphatic, alicyclic and aromatic groups containing between about 1–12 carbon atoms.

2. A smoking composition in accordance with claim 1 wherein the non-tobacco substitutes are selected from pectinaceous, cellulosic and other carbohydrate materials.

3. A smoking composition in accordance with claim 1 wherein at least one of R and $R^1$ in the carboxylate compound is an aliphatic group.

4. A smoking composition in accordance with claim 1 wherein at least one of R and $R^1$ in the carboxylate compound is an alicyclic group.

5. A smoking composition in accordance with claim 1 wherein at least one of R and $R^1$ in the carboxylate compound is an aryl group.

6. A smoking composition in accordance with claim 1 wherein one of R and $R^1$ in the carboxylate compound is an aryl group, and each of $R^2$ and $R^3$ is an alkyl group.

7. A smoking composition in accordance with claim 1 wherein the carboxylate compound is ethyl 2-propyl-3-hydroxy-3-methyl-3-phenylpropionate.

8. A smoking composition in accordance with claim 1 wherein the carboxylate compound is methyl 2,2-dimethyl-3-hydroxy-3-methyl-3-phenylpropionate.

9. A smoking composition in accordance with claim 1 wherein the carboxylate compound is ethyl 2-(2-butyl)-3-hydroxy-3-methyl-3-phenylpropionate.

10. A smoking composition in accordance with claim 1 wherein the carboxylate compound is ethyl 2-iospropyl-3-hydroxy-3-methyl-3-phenylpropionate.

11. A smoking composition in accordance with claim 1 wherein the carboxylate compound is ethyl 2-(2-butyl)-3-hydroxy-3-methylnonanoate.

12. A smoking composition in accordance with claim 1 wherein the carboxylate compound is ethyl 2-(2-butyl)-3-hydroxy-3-methyldodecanoate.

13. A method of preparing a smoking composition which is adapted to impart flavoring to the mainstream and sidestream smoke under smoking conditions, which method comprises incorporating into natural tobacco, reconstituted tobacco or non-tobacco substitute between about 0.00001 and 2 weight percent, based on composition weight, of a flavorant additive corresponding to the formula:

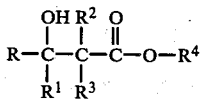

wherein R and $R^1$ are substituents selected from aliphatic, alicyclic and aryl groups containing between about 1-12 carbon atoms; $R^2$ and $R^3$ are hydrogen or substituents selected from aliphatic, alicyclic and aromatic groups containing between about 1-12 carbon atoms; and R and $R^1$ or $R^2$ and $R^3$, respectively, when taken together with connecting elements form an alicyclic structure; and $R^4$ is a substituent selected from aliphatic, alicyclic and aromatic groups containing between about 1-12 carbon atoms.

14. A method of improving the aroma imparted by the burning of a combustible article of manufacture within the environment of a human habitat, which method comprises incorporating into said article of manufacture prior to its combustion between about 0.001 and 10 weight percent, based on the weight of combustible content, of a hydroxy-substituted carboxylate compound corresponding to the formula:

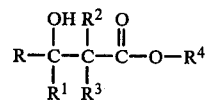

wherein R and $R^1$ are substituents selected from aliphatic, alicyclic and aryl groups containing between about 1-12 carbon atoms; $R^2$ and $R^3$ are hydrogen or substituents selected from aliphatic, alicyclic and aromatic groups containing between about 1-12 carbon atoms; and R and $R^1$ or $R^2$ and $R^3$, respectively, when taken together with connecting elements form an alicyclic structure; and $R^4$ is a substituent selected from aliphatic, alicyclic and aromatic groups containing between about 1-12 carbon atoms.

* * * * *

UNITED STATES PATENT AND TRADEMARK OFFICE
CERTIFICATE OF CORRECTION

PATENT NO. : 4,473,085
DATED : September 25, 1984
INVENTOR(S) : Harvey J. Grubbs et al It is certified that error appears in the above-identified patent and that said Letters Patent is hereby corrected as shown below:

Column 2, line 14, change "non-tabacco" to --non-tobacco--.

Column 7, line 41, change "Examinationof" to --Examination of--.

Column 11, line 6, change "62-hydrogen" to -- $\beta$ -hydrogen--.

Signed and Sealed this

Twenty-fifth Day of June 1985

[SEAL]

Attest:

DONALD J. QUIGG

Attesting Officer  Acting Commissioner of Patents and Trademarks